United States Patent [19]

Aslan et al.

[11] Patent Number: 5,610,526
[45] Date of Patent: Mar. 11, 1997

[54] CONTACT HAZARD METER HAVING A HUMAN EQUIVALENT CIRCUIT

[75] Inventors: Edward E. Aslan, Plainview, N.Y.; Om P. Gandhi, Salt Lake City, Utah

[73] Assignee: The Narda Microwave Corp., Hauppauge, N.Y.

[21] Appl. No.: 980,454

[22] Filed: Nov. 23, 1992

[51] Int. Cl.⁶ .......................... G01R 27/02; G01R 31/08
[52] U.S. Cl. .................. 324/522; 324/509; 324/520; 324/602; 324/692
[58] Field of Search ........................ 324/509, 510, 324/511, 520, 522, 555, 692, 693, 720, 602, 629; 174/5 R

[56] References Cited

U.S. PATENT DOCUMENTS

| | | | |
|---|---|---|---|
| 3,878,459 | 4/1975 | Hanna | 324/555 |
| 4,558,309 | 12/1985 | Antonevich | 324/509 X |
| 4,638,399 | 1/1987 | Maroney et al. | 324/509 X |
| 4,692,685 | 9/1987 | Blaze | 324/692 |
| 4,859,992 | 8/1989 | Hoigoard | 324/509 X |
| 5,001,436 | 3/1991 | Scot et al. | 324/689 |
| 5,068,619 | 11/1991 | Nakano et al. | 324/715 |

*Primary Examiner*—Maura K. Regan
*Assistant Examiner*—Glenn W. Brown
*Attorney, Agent, or Firm*—Hoffmann & Baron

[57] ABSTRACT

A contact hazard meter used to measure electromagnetic field induced currents which would flow through a human body to ground upon physical contact with an item carrying such field induced currents includes a conductive contact, a human equivalent circuit coupled to the conductive contact and an electronic circuit coupled to the human equivalent circuit for measuring and displaying a measurement of current flowing from the item and through the human equivalent circuit when the conductive contact is placed in physical contact with the item carrying the field induced currents. The human equivalent circuit approximates the impedance of the human body at varying frequencies. The contact hazard meter has a plurality of range settings, one setting providing the resultant current as a percentage of a safety guideline maximum permissible exposure value.

13 Claims, 8 Drawing Sheets

CONTACT HAZARD METER HAVING A HUMAN EQUIVALENT CIRCUIT

BACKGROUND OF THE INVENTION

1. Field of the Invention

The present invention relates to a metering device to measure current flowing through the human body, and more specifically relates to a metering device to measure current which would flow through the human body upon physical contact with an item carrying radio frequency, electromagnetic fields.

2. Description of the Prior Art

To reduce the potential for radio frequency (RF) shock and burns, safety guidelines with respect to human contact with items carrying radio frequency, electromagnetic fields require measurements of these contact currents. These measurements are required to ascertain whether the contact currents are lower than maximum permissible exposure values as set forth in the safety guidelines.

Limits on contact currents to reduce the potential for RF shock and burns have recently been proposed by the International Radiation Protection Association (IRPA) of the World Health Organization (WHO), in Canada and other foreign nations such as the United Kingdom. In the United States, the Institute of Electrical and Electronics Engineers (IEEE) C95.1- 1991 Standard has determined guidelines for contact currents which would flow through a human body to ground based on the condition of grasping an item carrying radio frequency, electromagnetic fields. The RF current (averaged over any one second) through an impedance equivalent to that of the human body should not exceed the following maximum permissible exposure (MPE) values:

$I_{MPE}=1000 \times f$ mA for $0.003 \leq f \leq 0.1$ MHz $I_{MPE}=100$ mA for $f > 0.1$ MHz where f is the frequency in megahertz (MHz).

For simultaneous exposure to electromagnetic fields at several frequencies where contact currents will exist for each of the frequencies, the proposed guidelines are that the fraction of the square of the contact currents in terms of $I^2_{MPE}$ should be determined for each of the frequencies and the sum of all such fractions should not exceed unity. This can be written as follows:

$$\sum_{i=1}^{n} \frac{I_i^2}{I_{MPE,i}^2} \leq 1$$

Due to the health hazards as determined by the previously mentioned organizations in the United States and abroad, with respect to human exposure to the potential for RF shock and burns, it is necessary for employers to monitor workers who are exposed to such hazards. Therefore, there is a need for a reliable, portable, accurate metering device for measuring contact current which would flow through the human body when physical contact is made with an item carrying radio frequency, electromagnetic fields. The metering device will let the operator know whether the current exceeds the maximum permissible exposure values as set forth in the proposed safety guidelines.

OBJECTS AND SUMMARY OF THE INVENTION

It is an object of the present invention to provide a metering device for measuring current which flows through the human body when in physical contact with an item carrying radio frequency, electromagnetic fields.

It is another object of the present invention to provide a metering device having a frequency-shaping circuit in conformity with the proposed ANSI safety guidelines with respect to maximum permissible exposure values.

It is a further object of the present invention to provide a metering device for measuring contact current flowing through the human body, the metering device having circuitry to provide a square root response as well as displaying the measured current in terms of a percentage of the IEEE C95.1 safety guideline.

It is a further object of the present invention to provide a contact current metering device which is portable and accurate over a wide frequency band of operation.

It is yet a further object of the present invention to provide a contact current metering device having a variable current range setting.

In accordance with one form of the present invention, the contact hazard meter for determining a current which would flow through a human body to ground in physical contact with an item carrying radio frequency, electromagnetic fields includes a conductive contact, a human equivalent circuit coupled to the contact and an electronic circuit coupled to the human equivalent circuit for measuring the current. The conductive contact is placed in physical contact with the item to be monitored. The current induced in the item being monitored carrying radio frequency, electromagnetic fields flows through the conductive contact and into the human equivalent circuit.

The human equivalent circuit consists of a network of resistors and capacitors which approximates the impedance of a human body at various frequencies. The human equivalent circuit is designed to approximate a worst case scenario of grasping contact with the item and the person having bare feet. The contact current flows through the human equivalent circuit and into an electronic circuit which measures the contact current and displays the resultant current on a meter.

The contact hazard meter in accordance with the present invention includes a current range select switch having four positions. The positions correspond to different current ranges: a 20 mA range, a 200 mA range, a percent of standard range and a 1000 mA range. In the 20 mA, 200 mA and 1000 mA ranges, the resultant current is displayed in milliamps. In the percent of standard range, the resultant current is displayed as a percentage of the IEEE C95.1 safety guideline maximum permissible exposure value.

For the percent of standard range, the electronic circuit includes a filter circuit which performs a frequency-shaping function so that the output signal from the filter circuit, which corresponds to the induced current flowing through the human equivalent circuit, varies linearly as a function or frequency below or equal to a predetermined frequency, and is constant (i.e., independent of frequency) above the predetermined frequency. The filter circuit also includes a diode which operates in the square law region to provide an output voltage signal which corresponds to the square of the current flowing through the circuit. These features of the filter circuit are important to meet the requirements of the IEEE guideline as well as to produce a resultant current in terms of percent of the IEEE C95.1 guideline maximum permissible exposure values.

For the 1000 mA range, the electronic circuit includes a timing circuit which permits current to flow through the human equivalent circuit for only a fraction of a second. The timing circuit is used to reduce the energy required to be dissipated by the components of the human equivalent circuit. The timing circuit includes a relay which is responsive to a switch for controlling the time period the contact current is permitted to flow. The switch for the relay is mounted within a non-conductive contact gun assembly which also houses the conductive contact.

The electronic circuit also includes a peak hold circuit for the 1000 mA range. The peak hold circuit is responsive to the timing circuit switch so that a charge proportional to the current flowing through the human equivalent circuit is stored in a capacitor of the peak hold circuit when current is permitted to flow. The peak hold circuit measures the stored charge on the capacitor.

The contact hazard meter in accordance with the present invention also includes a digital meter for displaying the resultant measured current.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
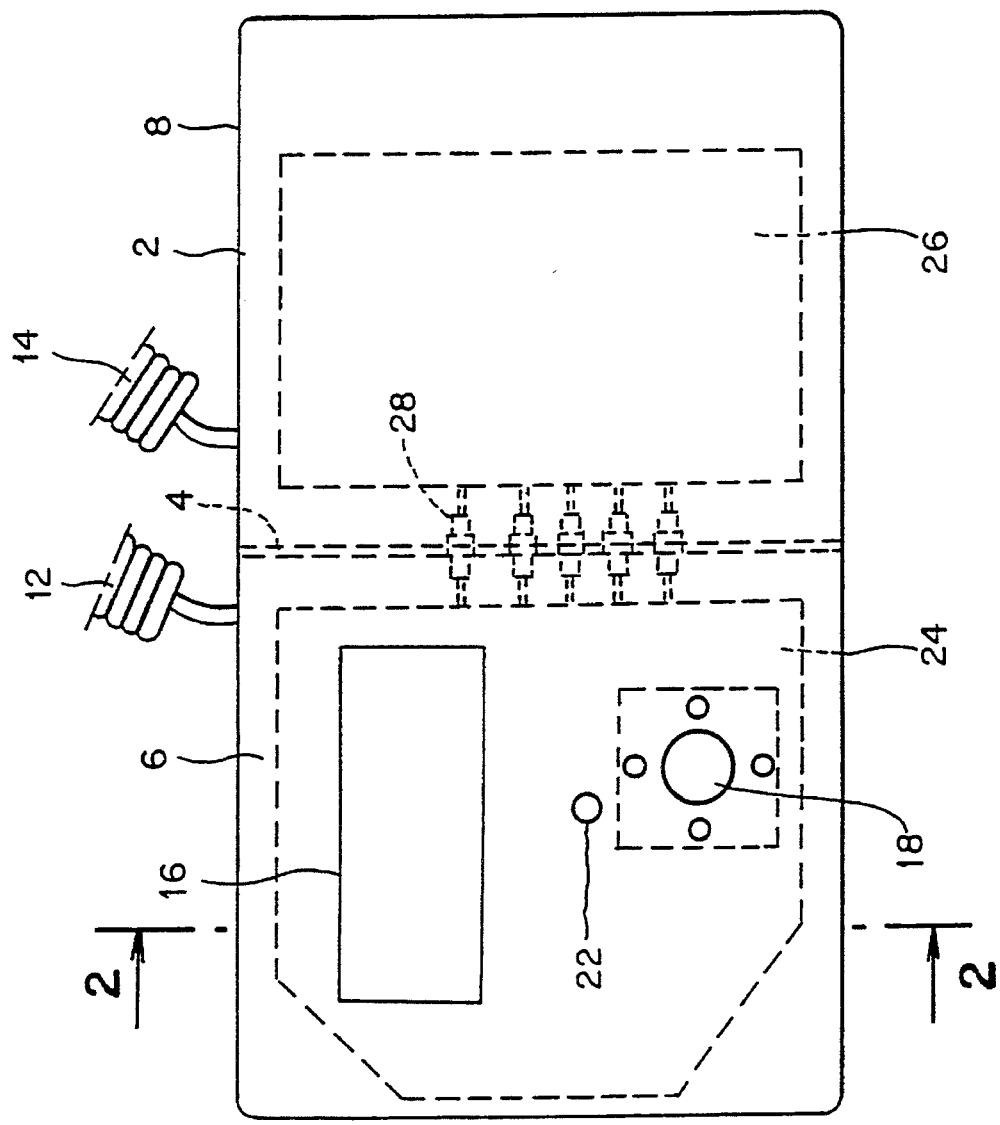
FIG. 1 is a top plan view of the contact hazard meter of the present invention.
Figure 2:
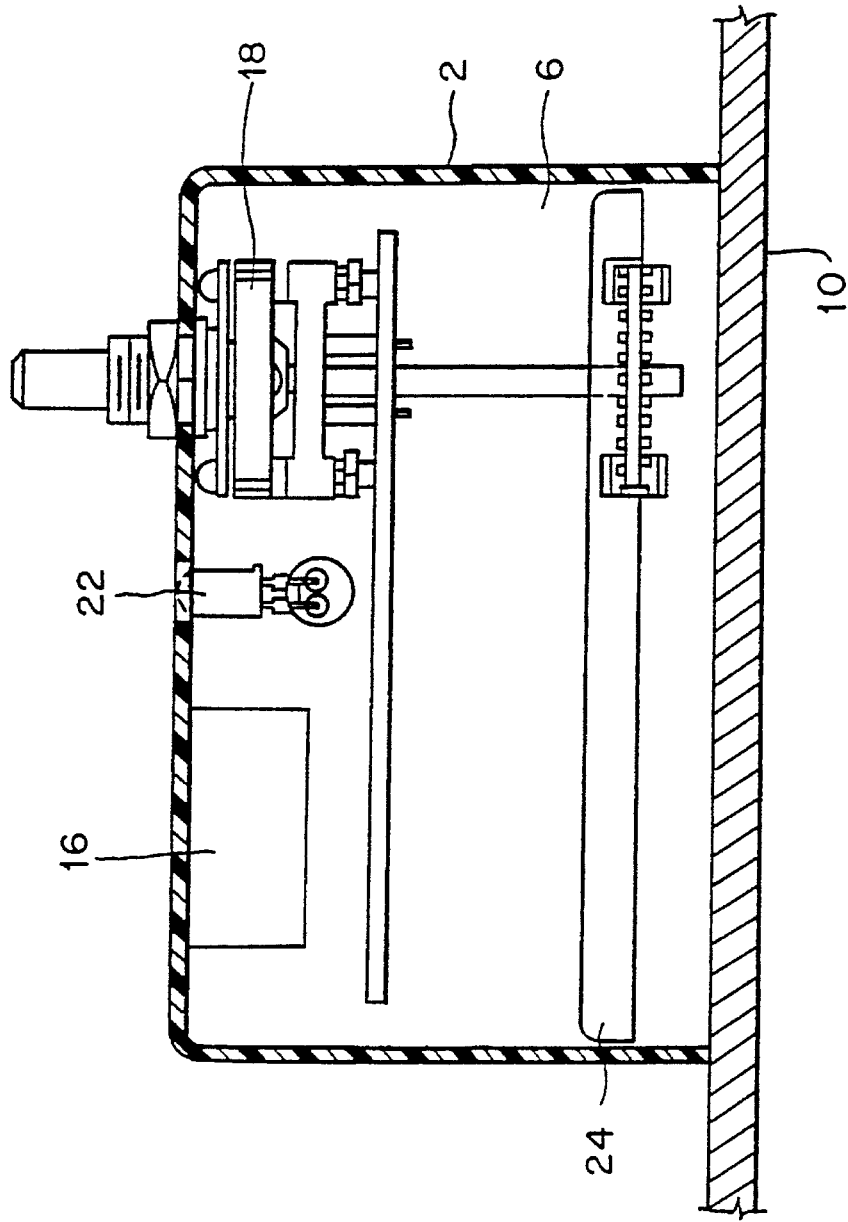
FIG. 2 is a cross-section of the contact hazard meter of the present invention taken along line 2—2, as shown in FIG. 1.
Figure 3:
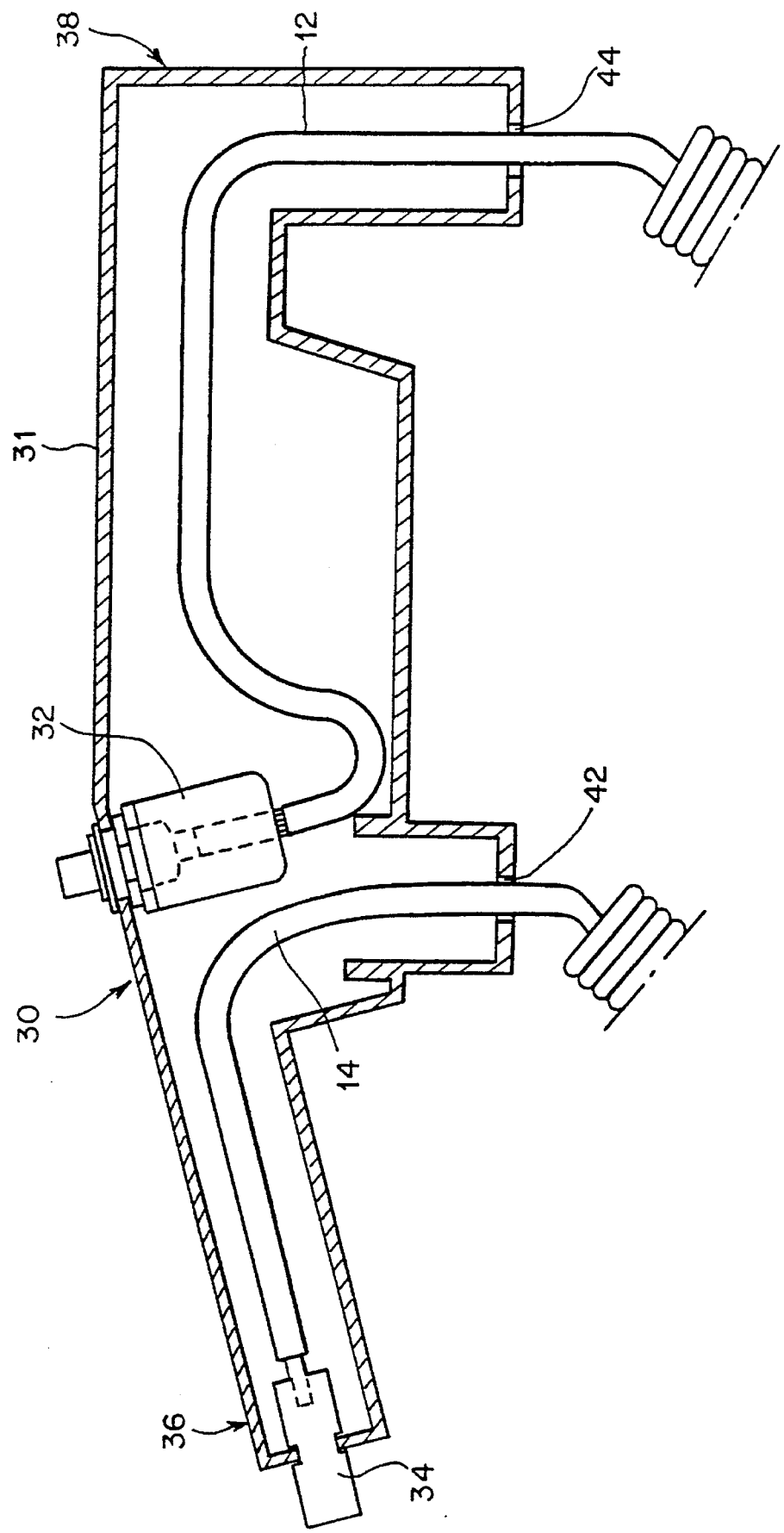
FIG. 3 is a longitudinal cross-sectional view of a contact gun assembly of the contact hazard meter of the present invention.

Referring to FIGS. 1–3 of the drawings, a contact hazard meter constructed in accordance with one form of the present invention includes a ground plate 10 which may be conveniently positioned near an item to be monitored. As illustrated in FIG. 1, a housing 2 is mounted to the ground plate 10 and includes two sections: a shielded section 6 and an unshielded section 8 which are separated by a shield wall 4. The shielded section 6 of the housing contains a shielded portion of an electronic circuit 24. Also mounted in the shielded section 6 of the housing 2 is a metering device 16 having a relatively large digital display, a ganged current range select switch 18 and a light emitting diode (LED) 22 which is part of the electronic circuit 24. Preferably, a coiled shielded lead 12 is connected at one end to the shielded electronic circuit 24 and to a contact gun assembly push-button switch at the other end.

The unshielded section 8 of the housing 2 contains an unshielded portion 26 of the electronic circuit. The shielded and unshielded portions of the electronic circuit, 24 and 26 respectively, are coupled together by a plurality of feed throughs 28 which pass through the shield wall 4. Preferably, a coiled unshielded lead 14 is connected at one end to the unshielded electronic circuit 26 and to a contact gun assembly conductive contact at the other end.

Referring to FIG. 2, a cross-section of the shielded section 6 of the housing 2 is illustrated. The housing 2 is substantially a five-sided box having a top and four lateral sides. The sides are mounted to the ground plate 10 which defines a bottom side of the housing. Since the electronics of the contact hazard meter of the present invention are mounted to the ground plate 10, the electronic circuits 24, 26 do not respond to scalar or potential fields. The ganged, multi-wafer range select switch 18 is mounted to the top of the housing 2 and comprises several switch sections, as will be described in greater detail, each section being switchable to four positions corresponding to four different contact current ranges. Also shown in FIG. 2 is the LED 22 which preferably extends through an opening in the top of the housing 2 so that it is visible to the operator of the contact hazard meter of the present invention.

FIG. 3 is a longitudinal cross-sectional view showing the internal components of a contact gun assembly 30 of the present invention. The contact gun assembly 30 includes a housing 31 having a first end 36 and a second end 38 opposite the first end, and is preferably formed from a non-conductive material such as plastic. Preferably, a highly conductive metal contact 34, such as a brass contact, is mounted in and extends through an opening formed in the first end 36 of the contact gun assembly housing 31. The unshielded lead 14 is coupled to the contact 34 and exits the contact gun assembly through a forward lead opening 42 formed in the housing 31. The unshielded lead 14 is preferably coiled once it has exited the contact gun assembly 30 and is coupled at its other end to the unshielded electronic circuit 26. The leads 14, 12 are coiled in order to maintain the leads from being in contact with the ground.

The contact gun assembly 30 of the present invention also includes a push-button switch 32 mounted on a top portion of the housing 31. The push-button switch 32 extends through an opening formed in the top portion of the contact gun assembly 30 and is coupled to the shielded lead 12. The push-button switch 32 is positioned between the first end 36 and second end 38 of the contact gun assembly housing 31. The shielded lead 12 exits the contact gun assembly 30 through a rear lead opening 44. The shielded lead 12 is preferably coiled once it has exited the contact gun assembly 30 and is coupled at its other end to the shielded electronic circuit 24. Preferably, the placement of the openings 42, 44 is such that the shielded and unshielded leads 12, 14 are maintained spaced apart from each other so that the shielded lead does not affect the line characteristics of the unshielded cable.

Figure 4:
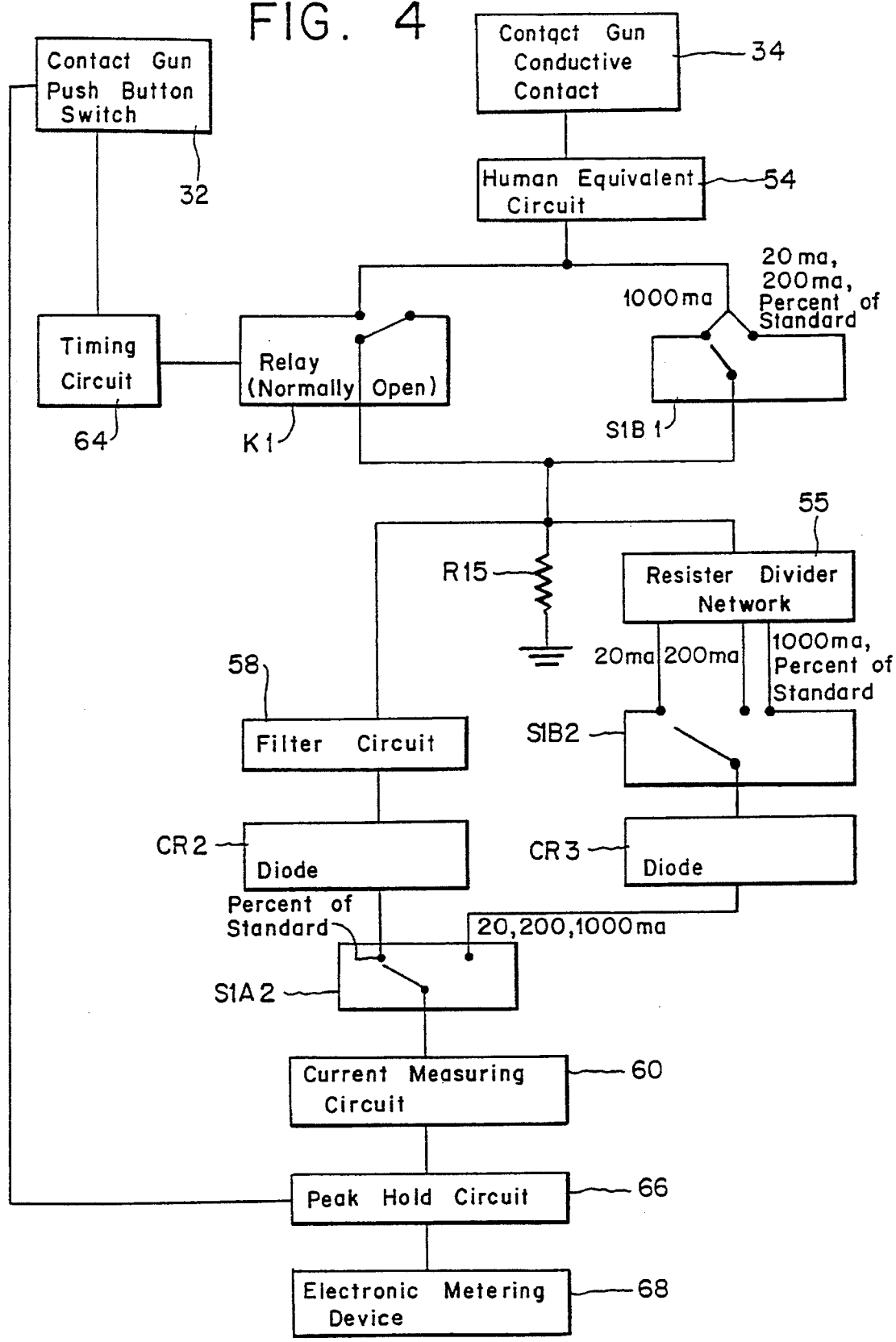
FIG. 4 is a block diagram of the various functional blocks of an electronic circuit formed in accordance with the present invention.

FIG. 4 is a block diagram illustrating the various components of the electronic circuitry for the contact hazard meter of the present invention. The operation of the electronic circuit depends upon a current range selected by the user. The contact hazard meter of the preferred embodiment uses the range select switch 18 to allow the user to select any one of four ranges: 20 milliamps (mA), 200 mA, 1000 mA and a range based upon an IEEE C95.1 safety guideline which is displayed as a percentage of a maximum permissible exposure value as set forth in the guideline.

To operate the contact hazard meter of the present invention, the user selects the desired current range using the range select switch 18 and places the contact hazard meter on the floor beside the item to be monitored. Thereafter, the contact gun assembly conductive contact 34 is placed in physical contact with the item being monitored. Any RF current induced in the item being monitored, hereinafter referred to as the contact current, flows through the conductive contact 34 and into the unshielded lead 14 which is in turn connected to a human equivalent circuit 54. A current will automatically flow into the human equivalent circuit 54 when a current range of 20 ma, 200 ma or the percent of standard range is selected. However, for the 1000 ma range, the user must press the push-button switch 32 while the gun assembly is in contact with the equipment being tested, which switch 32 and associated circuitry allow current to flow through the human equivalent circuit 54 for only a predetermined period of time.

The human equivalent circuit 54 is representative of the impedance of a human body in grasping contact with an item being monitored and the person having bare feet in contact with the ground. This is the worst case condition with respect to current flow through the human body to ground. The human equivalent circuit 54 has an impedance which has been designed to vary as a function of frequency, similar to the impedance of an actual human body, by using a network of resistors and capacitors. The accuracy of the human equivalent circuit 54 has been verified by comparing impedance values obtained by measurements performed on a number of volunteers at frequencies from 3 KHz to 30 MHz with the measured impedance values of the human equivalent circuit.

After the contact current passes through the human equivalent circuit 54, the range select switch section S1B1 allows the current to flow through a sensing resistor R15 in the 20 mA, 200 mA, and percent of standard current ranges. Switch section S1B1 is an open circuit in the 1000 mA mode. For the 1000 mA mode, current is permitted to flow only when the push-button switch 32 is pressed thereby closing the normally open contacts of a relay K1. When the relay contacts close, current flows through the human equivalent circuit 54 and into the sensing resistor R15.

The voltage developed across sensing resistor R15 is provided to a resistor divider network 55. Network 55 is provided to scale down the voltage across sensing resistor R15 caused by the contact current flowing through it from the human equivalent circuit 54. The resistor divider network 55 has three outputs on which are provided three scaled down output voltages corresponding to the 20 ma range, the 200 ma range and the 1000 ma range. The output voltages are provided to switch section S1B2, which is used to select one of the output voltages for measurement.

The scaled down output voltages generated by the resistor divider network are selectively provided through switch section S1B2 to a diode CR3 which operates in the square law region. The squared output signal from the diode CR3 is permitted to enter the current measuring circuit 60 when switch section S1A2 is in the 20 mA, 200 mA and 1000 mA position.

The voltage developed across the sensing resistor R15 by the contact current flowing through the resistor is also impressed upon the filter circuit 58 connected in parallel with resistor R15. Output voltage signal from the filter circuit 58 is provided to a diode detector CR2 which operates in the square law region, similar to the function performed by diode CR3 previously described.

The filter circuit 58 performs two basic functions. The first function is frequency-shaping and the second function is squaring the input signal. Frequency-shaping is performed by a resistor and capacitor network which operates to conform to the IEEE C95.1 safety guideline.

The IEEE C95.1 safety guideline defines a maximum permissible exposure (MPE) value which the RF current (averaged over any one second) flowing through a human body to ground should not exceed. The MPE values are as follows:

$I_{MPE}=1000 \times f$ mA for $0.003 \leq f \leq 0.1$ MHz    Eq. 1(a)

$I_{MPE}=100$ mA for $f>0.1$ MHz    Eq. 1(b)

where f is frequency in megahertz (MHz).

As required by the IEEE C95.1 safety guideline, the response of the frequency-shaping network is relatively independent of frequency for frequencies $f>0.1$ MHz and increases nearly linearly with frequency for the frequency band $0.003 \leq f \leq 0.1$ MHz satisfying Eq. 1(a) and 1(b).

For simultaneous exposure to electromagnetic (EM) fields at several frequencies where contact currents will exist for all these frequencies, the guideline proposes that the fraction of the squares of the contact currents in terms of $I^2_{MPE}$ should be determined for each of the frequencies. The sum of all such fractions should not exceed unity. This can be written as follows:

$$\sum_{i=1}^{n} \frac{I_i^2}{I_{MPE,i}^2} \leq 1 \qquad \text{Eq.2}$$

The second function of the filter circuit 58, the squaring of the input signal, occurs since the voltages encountered are relatively low due to the attenuation of the frequency-shaping network, thereby allowing the sensing diode CR2 connected to the filter circuit 58 to operate in the square law region. This function is needed to satisfy Eq. 2 of the IEEE C95.1 guideline with respect to simultaneous fields at several frequencies. Sensing diode CR2 squares the sum of the currents produced by all the frequencies present. This square law function also helps to combine the squares of voltages at different frequencies to obtain a composite dc voltage output signal from the filter circuit 58.

The output signal from the filter circuit diode CR2 is provided to the current measuring circuit 60 when switch section S1A2 is in the percent of standard position. The current measuring circuit 60 operates on the voltage signals provided to it by either the filter circuit or the resistor divider network to take effectively the square root of the sum of the squares of the frequency components comprising the signal to be measured. The current measuring circuit 60 is coupled to a peak hold circuit 66 which operates to amplify the signal. The peak hold circuit 66 is coupled to an electronic metering device 68 which includes a digital display. When the percent of standard range scale is selected, the electronicmetering device 68 displays the resultant current in terms of a percentage of the IEEE C95.1 safety guideline. When the 20 ma, 200 ma or 1000 ma range is selected, the metering device 68 displays a direct measurement in milliamperes of the contact current.

Another selection on the current range select switch 18 is the 1000 mA current range. The human equivalent circuit 54 used in accordance with the present invention preferably has a total impedance in the order of 300 ohms. Currents in the order of 1000 mA would require the dissipation of 300 watts of energy in the human equivalent circuit 54. Resistors having this high power rating would be prohibitively expensive and space consuming.

To overcome this problem, low power resistors are used; however, the current is allowed to flow through the human equivalent circuit 54 for only a fraction of a second, preferably about 0.1 seconds. This is accomplished using a push-button switch 32 located on the contact gun assembly which is in turn connected to a timing circuit 64. Recycle of the measuring procedure on this range scale is prevented for a period of approximately 5 to 10 seconds. This provides a duty factor of at least 50:1 (if current is permitted to flow for 0.1 seconds) thereby allowing a six watt resistor to be sufficient for energy dissipation where a 300 watt resistor would have been required if the current were permitted to continuously flow.

As previously mentioned, in the 1000 mA mode, no current flows through the human equivalent circuit 54 since the relay K1 which is coupled in series with the human equivalent circuit is in a normally open position. By placing the switch section S1B1 in the 1000 mA position, an open circuit is created which can be closed only by the operation of the relay K1. Current is permitted to flow through the human equivalent circuit 54 by pressing the push-button switch 32 of the contact gun assembly. The relay K1 is energized by a timing circuit 64 which changes the state of the relay K1 to a closed position for a fraction of a second thereby permitting current to flow from the item being monitored through the conductive contact 34 of the contact gun assembly and into the human equivalent circuit 54.

As previously described, the contact current flows through the sensing resistor R15. The voltage across resistor R15 is scaled down by the resistor divider network 55 and the output voltage from the resistor divider network 55 is squared by diode CR3. The squared signal flows through switch section S1A2 into the current measuring circuit 60. The current measuring circuit operates as previously described and provides the output signal to a peak hold circuit 66. As will be described in greater detail, the peak hold circuit includes a charging capacitor C20 and a diode CR5. A short across diode CR5 in the peak hold circuit 66 is opened when the push-button switch 32 is pressed thereby allowing the peak hold circuit 66 to store a charge on the charging capacitor. When the push-button switch is released, the diode CR5 in the peak hold circuit 66 is once again shorted, which effectively provides a low impedance across the capacitor so that the charge on the capacitor varies instantaneously with the input voltage provided to the peak hold circuit 66, and the metering device effectively displays the instantaneous current being measured. The peak hold circuit. also has a gain of approximately 10 so that the output signal is amplified before it is input into-the electronic metering device. The resultant signal is then displayed by the electronic metering device 68.

Figure 5:
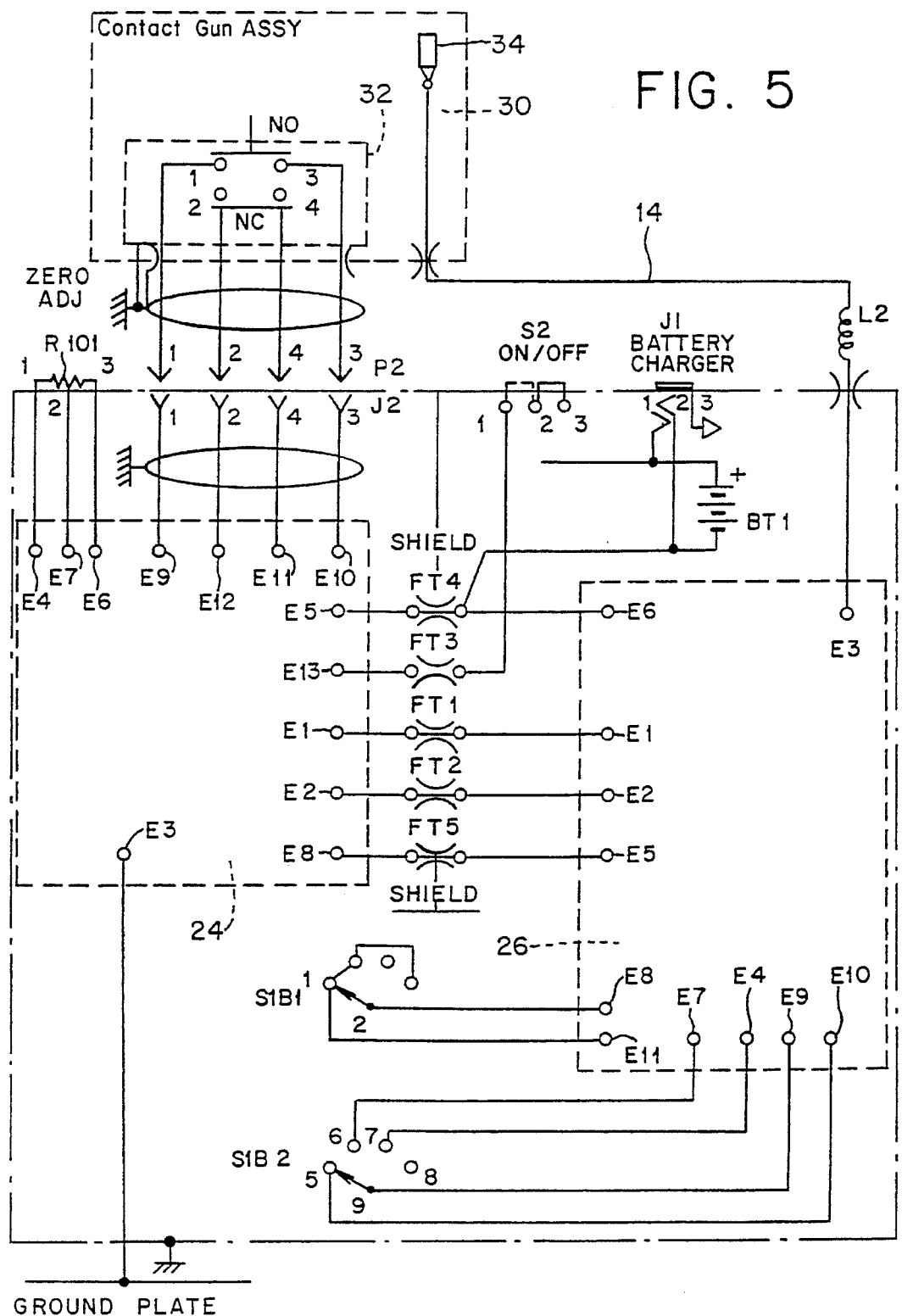
FIG. 5 is a schematic diagram of the contact gun assembly and circuit board assemblies of the contact hazard meter formed in accordance with a preferred embodiment of the present invention.
Figure 6:
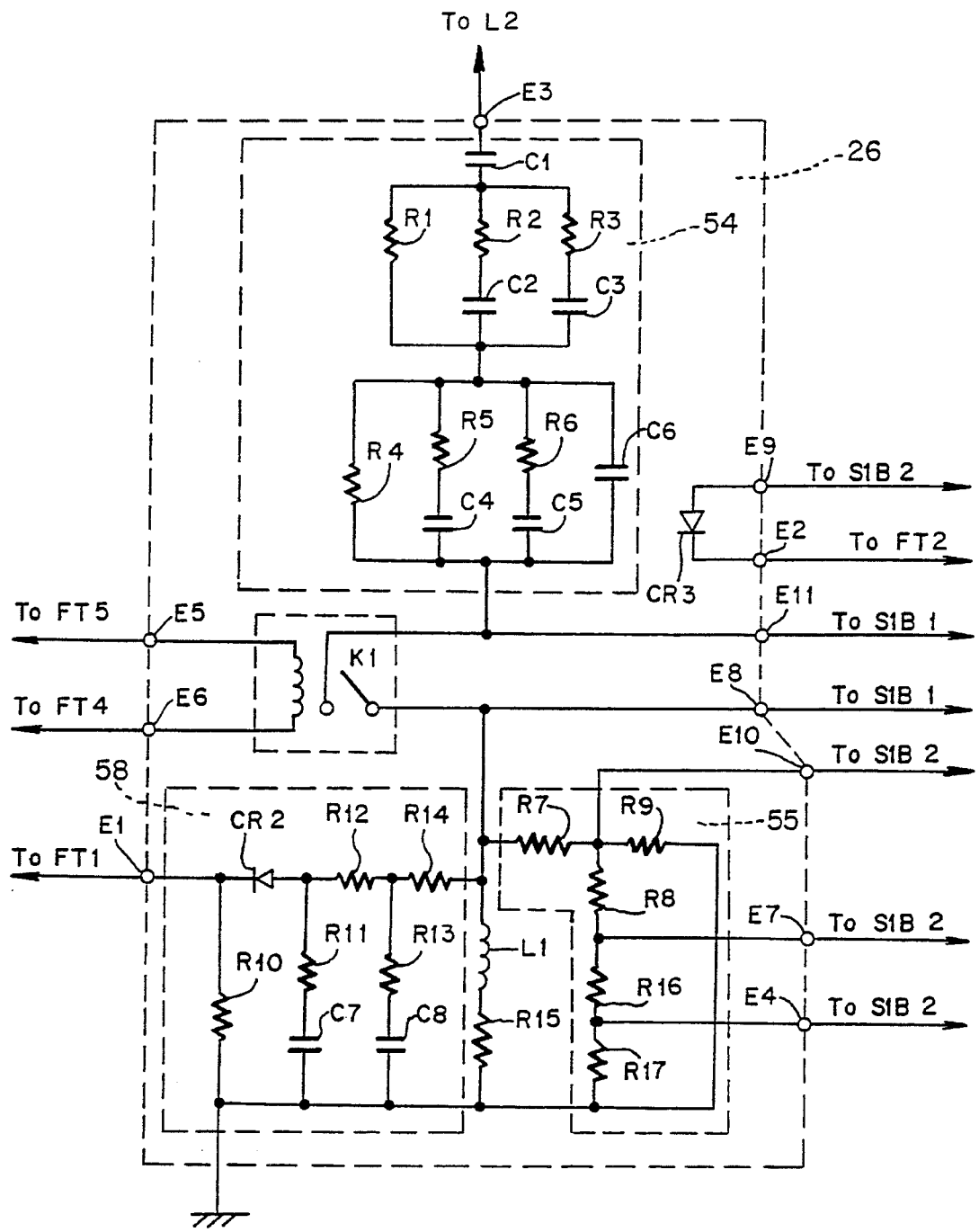
FIG. 6 is a schematic diagram of a human equivalent circuit, resistor divider network and filter circuit of the contact hazard meter formed in accordance with a preferred embodiment of the present invention.

FIGS. 5–7 illustrate one form of an electronic contact current measuring circuit for use with the contact hazard meter formed in accordance with the present invention. The actual values and part numbers of the components used in the electronic circuitry shown in FIGS. 5–7 are for illustrative purposes only and to facilitate an understanding of the invention. The operation of the circuit for each of the four selectable ranges will be now described in detail.

The components of the contact gun assembly 30 are schematically illustrated by FIG. 5. The conductive contact 34, preferably formed from a highly conductive material, is connected to an unshielded lead 14 which is preferably coiled from the contact gun assembly 30 to the contact hazard meter housing 2 to keep the lead from contacting the ground during use. The coiled lead 14 has series inductance L2 associated with it and is connected to terminal E3 of unshielded circuit board assembly 26.

The contact gun assembly 30 also contains push-button switch 32 having a pair of normally closed contacts and a pair of normally open contacts. More specifically, the push-button switch 32 has four terminals wherein terminals 1 and 3 are the normally open contacts and are connected to terminals E9 and E10, respectively, of the shielded circuit board assembly 24. Terminals 2 and 4 are the normally closed contacts and are connected to terminals E12 and E11, respectively, of the shielded circuits board assembly 24. The lead 12 connecting the push-button switch 32 to the shielded circuit board 24 is a multi-conductor shielded lead having a conductor connected to system ground.

The contact hazards meter of the present invention is powered by an internal rechargeable battery source, BT1 of approximately 9.0 volts. The internal battery source BT1 has connected to it an external jack J1 to which a battery charger may be connected for charging the internal battery BT1. In order to turn on the contact hazard meter of the present invention, a single pole, single or double throw switch S2 is located on a side of the housing 2. The on/off switch S2 includes three terminals 1, 2, 3 such that when the switch is positioned across terminals 2 and 3, the circuitry of the contact hazard meter is not energized. When the switch is positioned across terminals 1 and 2, positive voltage from the battery BT1 is provided through feed through FT3 to terminal E13 of the shielded circuit board assembly 24. The negative terminal of battery BT1 is connected to terminal E6 of the unshielded electronic circuit 26 and through feed through FT4 to terminal E5 of the shielded circuit board assembly 24. Terminal E5 provides a potential to a voltage regulator and a negative terminal of the electronic metering device, M1, as will be described in greater detail.

The shielded circuit board assembly 24 is coupled to the ground plate 10 by a preferably short conductor from terminal E3. The shielded circuit board assembly 24 is also connected to a potentiometer R101 which is used as a zero adjustment to correct for an integrated circuit ground which may not be at exactly zero potential. One leg of the potentiometer is connected to terminal E4, the other leg of the potentiometer is connected to terminal E6 and the wiper for the potentiometer is connected to terminal E7 of the shielded circuit board assembly 24.

Referring to FIG. 6, a schematic of the human equivalent circuit 54 is shown. The human equivalent circuit 54 is connected to input terminal E3 of the unshielded circuit board assembly 26 which is in turn connected to the conductive contact 32 of the contact gun assembly 30. Terminal E3 of the unshielded circuit board assembly 26 is connected to a capacitor C1 of the circuit 54 which is in turn connected to two series connected networks of resistors and capacitors. The first network includes three branches in parallel. The first branch includes resistor R1, the second branch includes resistor R2 and capacitor C2 in series, and the third branch includes resistor R3 and capacitor C3 in series.

The second network includes four branches connected in parallel. The first branch includes a resistor R4, the second branch includes a resistor R5 in series with a capacitor C4, the third branch includes a resistor R6 in series with capacitor C5 and the fourth branch includes a capacitor C6. The first and second parallel networks are connected in series along with capacitor C1 to form the human equivalent circuit 54. As previously described, the human equivalent circuit 54 is representative of the impedance of the human body as the impedance varies as a function of frequency. The impedance of the circuit corresponds to the impedance of a standing person from his hand to his bare feet, as if he were grasping the item being monitored, and having his bare feet in contact with the ground. This is the worst case scenario with respect to current flow through the human body to ground. The particular values selected for the components of the human equivalent circuit described above are set forth in the Parts List table to follow.

The human equivalent circuit 54 is connected to the current range select switch 18. The current range select switch 18 consists of five switch sections operating in unison, three switch sections being shown in the drawings with the designation S1A1, S1A2 and S1A3, and two switch sections being shown with the designation S1B1 and S1B2. Each switch section includes a wiper and four poles. The wipers associated with each switch section move concurrently to the selected position, as shown in the drawings. Each individual switch section performs a different function with respect to directing the various signals through the electronic circuit. For convenience, the four poles of each switch section, as shown in FIGS. 5–7, clockwise from the left most pole respectively represent the 20 ma, 200 ma, 1000 ma and the percent of standard current ranges.

The human equivalent circuit 54 is connected to output terminal E11 of the unshielded circuit board assembly 26. Terminal E11 is in turn connected to terminal 1 of the range select switch section S1B1 (FIG. 5). The wiper of the switch section S1B1 is connected at terminal 2 of the switch section which is in turn connected to terminal E8 of the unshielded circuit board assembly 26. The switch section S1B1 having its wiper positioned at terminal 2 is shorted in three positions, those positions corresponding to the 20 mA, the 200 mA and the percent of standard ranges. When the wiper is placed in the third position (i.e., the 1000 mA position), the switch section forms an open circuit between the human equivalent circuit 54 and the current measuring and filter circuits 60, 58 to follow. Relay K1, which is effectively connected in parallel with switch section S1B1, when activated will allow the contact current to flow into a current sensing resistor R15 for a predetermined period of time, as will be described in greater detail. The short circuit created by the switch section in the 20 ma, 200 ma and percent of standard range three positions creates a short with respect to relay K1 which only operates in the 1000 mA range. Thus, relay K1 is bypassed when the contact hazard meter is operating in the 20 mA, 200 mA and percent of standard modes.

The contact current, which is adjusted by passing through the human equivalent circuit 54, flows through switch section S1B1 or, alternatively, the switching circuit of relay K1, into a current sensing resistor R15 as illustrated in FIG. 6. A resistor divider network 55 is also connected in parallel with sensing resistor R15 as illustrated in FIG. 6 by the dashed box to the right of the sensing resistor. Preferably, an inductor L1 is coupled in series with sensing resistor R15. Inductor L1 is provided and is selected with a particular inductance to compensate for the inductance of the lead line between the contact gun assembly and the unshielded circuit assembly, as the lead line inductance affects the high frequency performance of the contact hazard meter and, therefore, should preferably be compensated for.

The resistor divider network 55 is provided to scale down the voltage across the sensing resistor R15 caused by the contact current flowing through it from the human equivalent circuit 54. The resistor divider network is used when the contact hazard meter of the present invention is operating in the 20 mA, 100 mA or 1000 mA modes.

More specifically, the resistor divider network 55 includes the series connection of resistors R7, R8, R16 and R17, in succession, and resistor R9 coupled in parallel across the series connection of resistors R8, R16 and R17. One end of resistor R7 is connected to one end of inductor L1, and one end of resistor R17 is connected to one end of sensing resistor R15 as well as to ground.

The values of the resistors of the resistor divider network 55 are selected so that the voltage developed across sensing resistor R15 by the contact current is proportionally scaled down in accordance with the current range selected by the user of the contact hazard meter. The values of the resistors, and in particular, resistor R7, are also chosen so as not to load down sensing resistor R15.

The connection between resistor R7 and resistor R8 is provided to terminal E10 of the unshielded circuit assembly 26 which is provided with an output voltage proportional to the voltage across sensing resistor R15 but scaled down for operation in the 20 mA mode. Similarly, the junction between resistors R8 and R16 is provided to terminal E7 of assembly 26, which is provided with an output voltage proportional to the voltage across sensing resistor R15 but even more attenuated than the output voltage on terminal E10 for operation of the contact hazard meter in the 200 mA mode. Also, the juncture between resistors R16 and R17 is provided to terminal E4. The output voltage on terminal E4 is proportional to the voltage across sensing resistor R15 and it is the most attenuated voltage resulting from the resistor divider network 55 for operation in the 1000 mA mode.

Terminals E10, E7 and E4 of the unshielded circuit assembly 26 are respectively provided to poles 5, 6 and 7, respectively, of range switch section S1B2 (FIG. 5), and the wiper (terminal 9) of switch section S1B2 is provided to terminal E9 of the unshielded circuit assembly 26.

The unshielded circuit assembly 26 includes a diode detector comprising diode CR3 (FIG. 6) having its anode connected to input terminal E9 and its cathode connected to output terminal E2 of the unshielded circuit assembly 26. Accordingly, the scaled down output voltages generated by the resistor divider network are selectively provided through switch section S1B2 to diode CR3. Because of the relatively small currents provided to the diode CR3 by the resistor divider network 55, diode CR3 operates in the square law region. The diode detector CR3 squares the sum of all of the current components produced by a multiple frequency field.

Figure 7A:
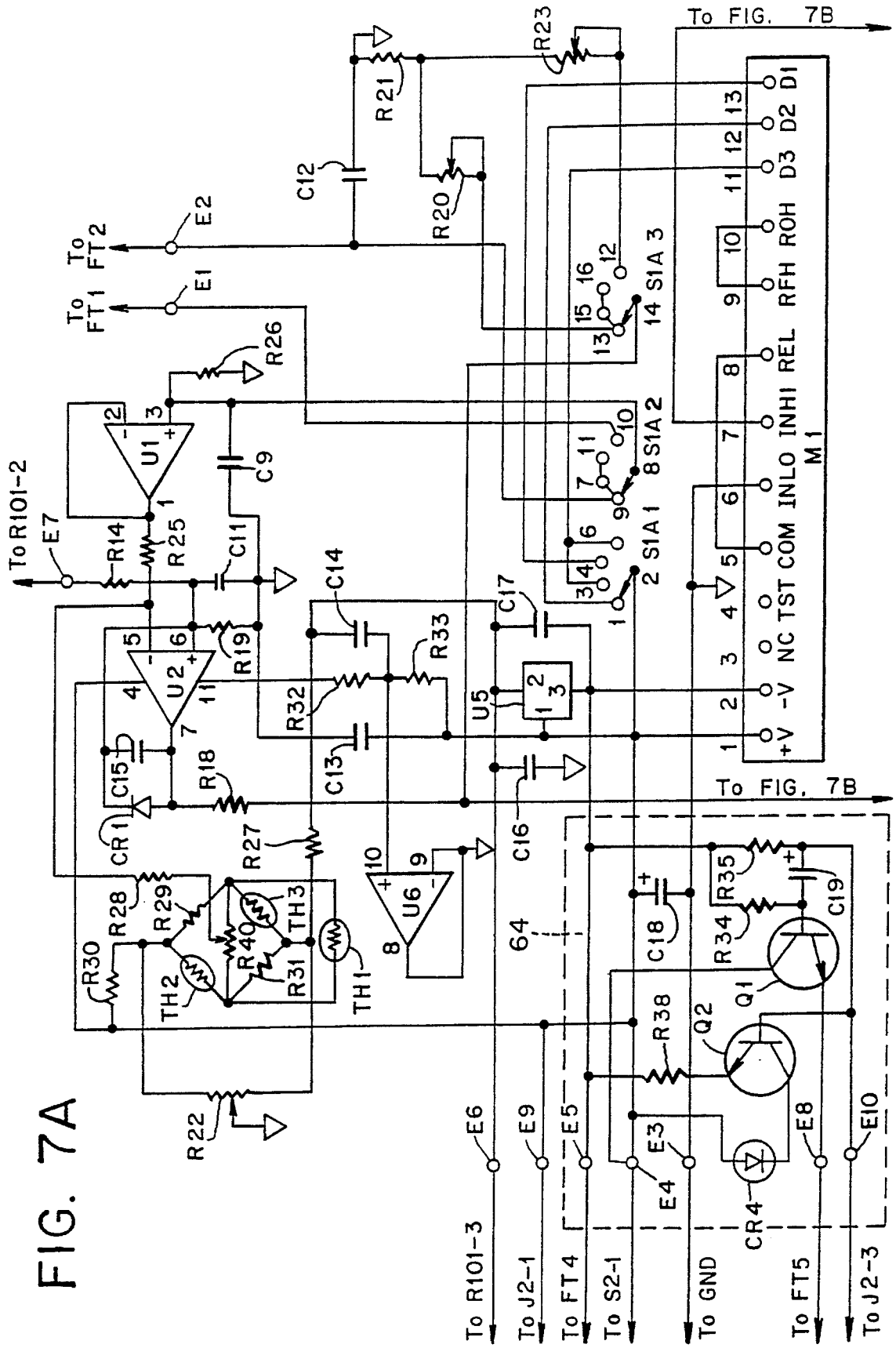
FIGS. 7A and 7B are schematic diagrams of a current measuring circuit, timing circuit and peak hold circuit of the contact hazard meter formed in accordance with a preferred embodiment of the present invention.

The output signal from the diode detector (i.e., diode CR3) at output terminal E2 is provided through a feed through FT2 to terminal E2 of the shielded circuit assembly 24 (FIG. 7A). Input terminal E2 of the shielded circuit assembly is provided to poles 9, 7 and 11 of switch section S1A2, whose wiper (terminal 8) is connected to the non-inverting input (pin 3) of operational amplifier U1, which acts as a buffer amplifier and forms part of the current measuring circuit 60, as will be described in greater detail.

When switch section S1A2 is placed in the percent of standard range, a voltage signal, shaped by the filter circuit 58 is provided to the current measuring circuit 60. As previously described, the filter circuit 58 performs two functions, the first function being a frequency-shaping function and the second function being a square law function. These functions were described in greater detail in reference to FIG. 4 illustrating the circuit block diagram of the present invention. The filter circuit 58 includes three branches connected in parallel: the first branch includes a resistor R13 in series with a capacitor C8; the second branch includes a resistor R11 in series with a capacitor C7; and the third branch includes a resistor R10. A resistor R14 is connected between sensing resistor R15 and the first branch of the filter circuit 58 and a resistor R12 is connected between the first branch and the second branch of this circuit. The parallel resistor and capacitor branches have an impedance which varies as a function of frequency. More specifically, as the frequency decreases, the reactance of the capacitors increases to a magnitude where it exceeds the resistance of the resistors such that the resistance of the resistors is negligible when compared to the reactance of the capacitors. Conversely, as the frequency increases, the reactance of the capacitors decreases so that their effect is negligible in the circuit.

Positioned between the second branch and third branch of the filter circuit is a diode detector CR2 which operates as a sensing diode for the contact current. The diode detector CR2 is provided with currents of relatively small magnitude so that the diode operates in the square law region in order to satisfy the multiple frequency equation set forth in the IEEE C95.1 guideline. The diode detector operates to combine the squares of voltage components at different frequencies to obtain a composite voltage output signal from the filter circuit. The output signal from the diode detector CR2 is provided from terminal E1 through feed through FT1 to terminal E1 of the shielded circuit assembly 24. Input terminal E1 of the shielded circuit assembly is provided to pole 10 of switch section S1A2, whose wiper (terminal 8) is connected to the non-inverting input (pin 3) of operational amplifier U1, which is part of the current measuring circuit 60.

Figure 7B:
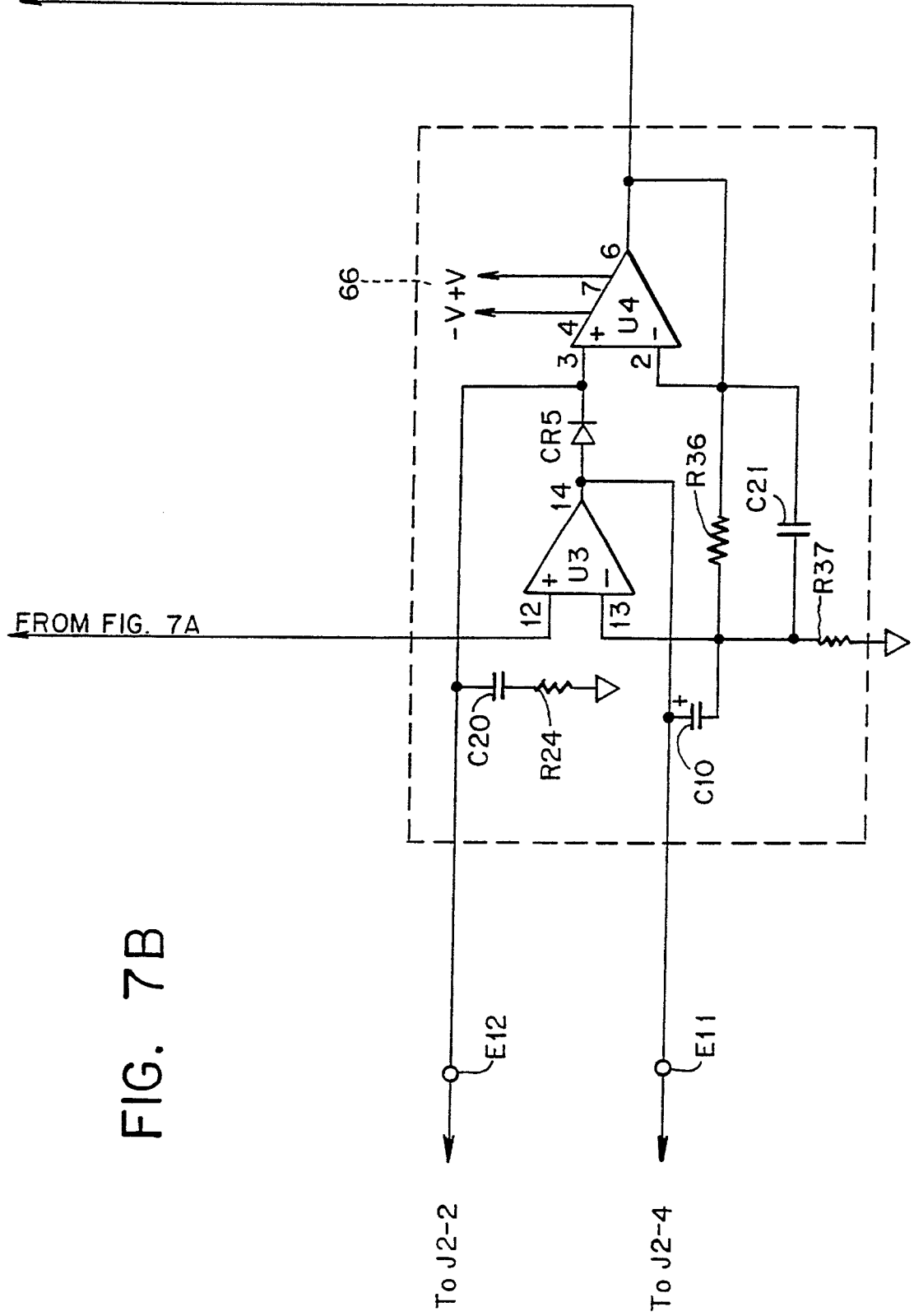

After the voltage signal corresponding to the contact current is summed and squared by the diode detectors, CR2 in the percent of standard mode and CR3 in the 20 mA, 200 mA and 1000 mA modes, the signal enters the current measuring circuit 60 which is schematically illustrated in FIGS. 7A and 7B. The squared output signal is provided through the wiper of switch section S1A2 to the non-inverting input of operational amplifier U1.

Operational amplifier U1 operates as a unity gain buffer or voltage follower amplifier which is used to reduce the output impedance and buffer the filter circuit 58 and resistor divider network 55 with a high impedance. The output of operational amplifier U1 (pin 1) is fed back to the inverting input of the operational amplifier at pin 2. Also, one leg of a filtering capacitor C9 and one leg of a resistor R26 are connected to the non-inverting input of operational amplifier U1 at pin 3. The other legs of the capacitor C9 and resistor R26 are connected to system ground.

The output of unity gain buffer or follower amplifier U1 (pin 1) is connected to one leg of a current limiting resistor R25 whose other leg is coupled to the non-inverting input of a second operational amplifier U2 at pin 5. The non-inverting input of operational amplifier U2 is also connected to one leg of a current limiting resistor R28, the other leg of resistor R28 being connected to the wiper of a potentiometer R40 which is part of a temperature compensation circuit in a bridge configuration, as will be described in greater detail.

The inverting input (pin 6) of U2 is connected to one leg of a resistor R14 which is in turn connected to terminal E7 of the shielded board assembly 24. As previously described, terminal E7 of the shielded circuit board assembly is connected to the wiper of a zero adjustment potentiometer R101. The inverting input of operational amplifier U2 is also connected to a parallel connected filtering network which includes a capacitor C11 and a resistor R19 whose other legs are connected to ground.

operational amplifier U2 along with diode CR1, which is part of the feedback circuit of operational amplifier U2, form a square root circuit to take the square root of the sum of the squares of the signals produced by either diode detector CR2 or CR3, depending upon the current range selected. The output of operational amplifier U2 (pin 7) is connected to the anode of diode CR1 and one leg of a capacitor C15 connected in parallel to the diode. The output from the cathode of diode CR1 is fed back into the inverting input of operational amplifier U2 at pin 6. The capacitor C15, having its other leg connected to the inverting input of operational amplifier U2, is provided to prevent oscillations at the lower end of the frequency band. A reference potential is applied to operational amplifier U2 at pin 4 through switch S2 at terminal 1. Pin 4 of operational amplifier U2 is also connected through terminal E4 of the shielded circuit assembly 26 to the zero adjustment potiometer R101.

As previously noted, the diode CR1 along with operational amplifier U2 performs the square root function in the feedback circuit of operational amplifier U2. This is necessary since the signal at this stage is proportional to $$\sum_i I_i^2/I_{MPE,i}^2.$$

For example for a single frequency this implies a signal proportional to $I_c^2/I_{MPE}^2$ where $I_c$ is the contact current. Taking the square root provides the desired ratio of $I_c/I_{MPE}$.

The gain of operational amplifier U2 is preferably greater than 1 and is equal to 1 plus the resistance of CR1 divided by the input resistance, R19. The output of operational amplifier U2 (pin 7) is also connected to one leg of a limiting resistor R18, and the other leg of resistor R18 is connected to switch section S1A3 at its wiper (terminal 14). Terminals 13, 15, and 16 of switch section S1A3 are shorted together and are coupled to a potentiometer R20 having its other leg connected to a resistor R21 which is coupled to system ground. Potentiometer R20 is used to provide an independent gain adjustment for the 20, 200, and 1000 mA ranges. In the percent of standard range, the wiper of switch section S1A3 is coupled to terminal 12 of S1A3. Similarly, terminal 12 is coupled to a potentiometer R23 which is connected to resistor R21 coupled to system ground. Potentiometer R23 is provided to adjust the gain of the circuit in the percent of standard mode. Independent gain adjustment is required since the diode detectors, CR2 and CR3, may have different operating characteristics. Capacitor C12 is connected between ground and the cathode of diode CR3 for filtering the signal detected by diode CR3.

The output of operational amplifier U2 (pin 7) is also coupled to the non-inverting input of operational amplifier U3 which is part of the peak hold circuit 66 which will be described in greater detail.

As previously described, the non-inverting input of operational amplifier U2 is coupled to the wiper of R40 through a resistor R28. Potentiometer R40 is part of a temperature offset compensation circuit in a bridge configuration. Due to the small signal operation of the current sensing diodes CR2 and CR3, the output of these diodes may change significantly with temperature variations. The temperature compensating circuit corrects for offset produced by ambient temperature changes. The temperature compensation circuit includes a pair of thermistors TH2 and TH3 connected in a bridge configuration with bridge resistors R29, R31. The junction between the thermistor TH2 and resistor R29 and thermistor TH3 and resistor R31 are respectively coupled to the legs of potiometer R22 whose wiper is connected to ground. Also connected to the junction between thermistor TH2 and resistor R29 is a positive voltage from switch S2 (terminal 1) through a limiting resistor R30. The junction between thermistor TH3 and resistor R31 is coupled through a limiting resistor R27 to a negative output of a voltage regulator U5. The junction between thermistor TH2 and resistor R31 and thermistor TH3 and resistor R29 are respectively connected to the opposite legs of potentiometer R40, whose wiper is coupled to the non-inverting input of amplifier U2. Potentiometer R22 is adjusted at ambient temperature for zero voltage offset and potentiometer R40 is adjusted for zero offset at elevated temperatures. Once adjusted, the thermistors TH2, TH3 in the bridge configuration maintain the balanced temperature compensation. The temperature compensation circuit also includes a third thermistor TH1 connected across inner bridge potentiometer R40. Thermistor TH1 helps to balance and compensate for colder temperatures. Due to the diode characteristics of diode CR1 and diode CR2 or CR3, as temperature decreases, a greater offset is incurred and this offset is compensated for by thermistor TH1. The thermistor bridge circuit is described in U.S. Pat. No. 4,605,905, entitled, "Amplifier Input Circuitry with Compensation for Pyroelectric Effects" which issued on Aug. 12, 1986, the disclosure of which is incorporated herein by reference.

Following temperature compensation and after passing through the square root circuitry of operational amplifier U2 and diode CR1, the output signal is input into the non-inverting input of operational amplifier U3 at pin 12 (FIG. 7B). Operational amplifiers U3 and U4, diode CR5, charging capacitor C20 and several other resistors and capacitors make up the network previously mentioned as the peak hold circuit 66. However, diode CR5 is normally shorted by a normally closed contact on the push-button switch 32, thereby not permitting charging capacitor C20 to store a charge and allowing normal metering to take place when the range select switch 18 is in the 20 mA, 200 mA and percent of standard modes. The circuit operates as a peak hold circuit in the 1000 mA mode only. When the push-button switch of the contact gun assembly is pressed, thereby opening the short across the diode CR5, a charge is permitted to be stored on the charging capacitor C20.

The output of operational amplifier U3 (pin 14) is connected to the anode of the diode CR5, the cathode of diode CR5 being connected to the non-inverting input of operational amplifier U4 (pin 3). Diode CR5 is normally shorted by leads connected to terminals E11 and E12 of the shielded circuit which are connected to the normally closed contact terminals 2, 4 of the push-button switch 32. Two reference voltages, a negative voltage and a positive voltage, are applied to operational amplifier U4 at pins 4 and 7, respectively.

The output of operational amplifier U4 is connected to a resistor R36 and fed back into the inverting input of operational amplifier U1 (pin 13). The inverting input of operational amplifier U1 is also connected to a resistor R37 whose other leg is connected to ground. Therefore, the gain of operational amplifier U3 is equal to the resistance of R36 plus the resistance of R37 divided by the resistance, of R37. The values of the resistors have been chosen to provide operational amplifier U3 with a gain of approximately 10. Since the peak hold circuit provides an increase in gain, it also includes two capacitors C21 and C10 to prevent oscillations of the signal. Capacitor C21 is connected in parallel to resistor R36 and capacitor C10 is coupled at one end to the output of operational amplifier U3 and at the other end to one leg of resistor R37 whose other leg is connected to ground.

The resultant output signal from operational amplifier U4 (pin 6) is connected to the input of the meter, M1 at terminal 7 of the meter. The meter M1 then displays the resultant current based upon the range selected. The output is also fed back into the inverting input at pin 2 of amplifier U4. Operational amplifier U4 operates as a high impedance buffer amplifier having unity gain.

The current measuring circuit 60 of the contact hazard meter of the present invention is provided with a regulated ±2.5 volt supply voltage. An integrated circuit (IC) voltage regulator U5 in conjunction with an operational amplifier U6 and filtering resistors and capacitors connected to the internal battery BT1 provide the regulated dual voltages. The input of IC voltage regulator U5 (pin 3) is coupled through feed through FT4 to the negative terminal of battery BT1. Pin 3 of voltage regulator U5 is also connected to the negative voltage terminal (terminal 2) of the electronic metering device, M1. The voltage regulator U5 has a common at pin 1 which is used as a reference with respect to the input (pin 3) and output (pin 2) voltages. The output of the voltage regulator provides a voltage which is 5 volts lower than the voltage at the reference or common (pin 1) or in this case, a regulated −2.5 volts. The reference voltage at pin 1 is equal to +2.5 volts, approximately five volts less than the positive terminal voltage of battery BT1. Pin 1 of voltage regulator U5 is coupled to the positive terminal of battery BT1 through switch S2 at terminal 1 of the switch. Pin 1 of regulator U5 is also connected to the positive terminal (terminal 1) of the meter, M1.

The regulated voltage output at pin 2 of regulator U5 is coupled to a parallel connected filtering network including a capacitor C14 and a resistor R32 whose other legs are connected to the non-inverting input of operational amplifier U6. The output of the operational amplifier is fed back into the inverting input at pin 9 as well as being coupled to ground. A resistor R33 has one leg connected to pin 1 of the regulator U5 and the other leg connected to the non-inverting input of amplifier U6, and a capacitor C13 has one leg coupled to ground and its other leg coupled to pin 1 of the regulator U5. Operational amplifier U6, being thus connected to the junction of resistors R32 and R33, creates a virtual ground within the regulated voltage supply circuitry so that a positive regulated voltage and a negative regulated voltage, with respect to the virtual ground may be realized. The voltage regulating circuit also contains two filtering capacitors C16 and C17. Capacitor C17 shunts the input and output of the voltage regulator and capacitor C16 is connected at one end to pin 2 of the regulator U5 and its other leg connected to ground. Both capacitors C16, C17 provide stability and prevent oscillation in the regulated voltage supplied to the circuit.

Referring to FIGS. 6 and 7, when the range select switch 18 is placed in the 1000 mA mode, a timing circuit 64 using a relay K1 is operated to restrict the current flow through the circuit to only a fraction of a second. The timing circuit 64 includes the push-button switch 32 located on the contact gun assembly 30, as previously described. Pressing the push-button switch 32 energizes transistor Q1 which in turn energizes the relay K1 for a predetermined time period. The contacts of relay K1 close permitting current to flow into the conductive contact 34 of the contact gun assembly 30 and through the human equivalent circuit 54. The current then flows through the resistor divider network 55 as previously described and into the current measuring circuit 60 at the non-inverting input of buffer or follower operational amplifier U1 at pin 3.

Pressing the push-button switch 32 also opens the normally closed contact of the push-button switch 32 thereby opening the short across diode CR5 positioned between the output of operational amplifier U3 and the non-inverting input of operational amplifier U4 of the peak hold circuit 66. Upon opening the short across diode CR5, a charge is stored on the charging capacitor C20 of the peak hold circuit 66. When the push-button switch 32 is released, diode CR5 is once again shorted and metering reverts from peak hold to a measurement of the instantaneous contact current.

More specifically, the timing circuit 64 includes NPN transistors Q1 and Q2. Transistor Q1 controls the energization of relay K1, while transistor Q2 controls the illumination of the "measurement ready" light, LED CR4.

The emitter of transistor Q1 is coupled to one end of the coil of relay K1 through circuit board terminal E8 and feed through FT5. The other end of the relay coil is effectively connected to the negative side of the circuit battery. The collector of transistor Q1 is coupled to the positive side of the battery through board terminal E4 and on/off switch S2.

The base of transistor Q1 is connected to one end of resistor R34, whose other end is connected to the negative side of the battery through circuit terminal E5 and feed through FT4. The base of transistor Q1 is also connected to one end of a capacitor C19. The other end of capacitor C19 is coupled to one end of a resistor R35 and to one pole (terminal 3) of the normally open section of push-button switch 32, through circuit board terminal E10. The other end of resistor R35 is coupled to the negative side of the battery. The other pole (terminal 1) of the normally open section of switch 32 is coupled to the positive side of the battery.

Capacitor C19 and resistor R34 together define a timing circuit having a first time constant, and capacitor C19 and resistor R35 (and resistor R34, which has a much smaller resistance value than resistor R35) define another timing circuit with a second time constant. When the push-button switch 32 is pressed, battery voltage is provided to capacitor C19 and resistor R34, turning on transistor Q1. Transistor Q1 conducts current and energizes relay K1, allowing current to flow through the human equivalent circuit 54. In the meanwhile, capacitor C19 charges relatively rapidly due to the first time constant defined by capacitor C19 and resistor R34. When finally charged, capacitor C19 turns off transistor Q1 which, in turn, deenergizes relay K1.

When the push button switch 32 is released, no more voltage is provided to capacitor C19. Capacitor C19 then discharges through resistor R35 (and resistor R34) at a much slower rate (i.e., the second time constant), maintaining transistor Q1 in a cut off state. The first time constant allows current to flow through the human equivalent circuit 54 for only a fraction of a second, while the second, longer time constant ensures that the duty cycle of the circuit is such that very little power is dissipated by the components of the human equivalent circuit so that lower wattage components may be used.

Transistor Q2, which powers the LED CR4, has its emitter coupled to the negative side of the battery and its collector connected to the cathode of the LED. The anode of LED CR4 is coupled to the positive side of the battery through the on/off switch S2. The base of transistor Q2 is coupled to the juncture of resistor R35 and capacitor C19.

When the push button switch 32 is pressed, transistor Q2 is forward biased, allowing current to flow through LED CR4. LED CR4 remains illuminated. When the push-button switch 32 is released, transistor Q2 remains forward biased and on, due to capacitor C19 discharging through resistor R35, and turns off when capacitor C19 is discharged. The LED CR4 will then go off, indicating to the user that another measurement in the 1000 ma range may be made.

As previously described, the normally closed contact of push-button switch 32, at terminals 2 and 4 of the switch, is connected to the peak hold circuitry 66 so that one terminal is connected to the anode of diode CR5 and the other terminal is connected to the cathode of diode CR5 in order to create the short across the diode in all ranges except the 1000 mA range. Also connected to terminal 2 of the normally closed contact of the push-button switch 32 is one leg of the charging capacitor C20. The other leg of the charging capacitor C20 is connected to a resistor R24 which is in turn connected to system ground. When the push-button switch 32 is pressed, the switch removes the short across diode CR5 so that a charge is stored on charging capacitor C20 and retained by the peak hold circuit 66. The operational amplifier U4 of the peak hold circuitry 66 provides an amplified voltage output signal corresponding to the charge stored on the capacitor to the electronic metering device M1 at terminal 7 of the meter. When the push-button switch 32 is released, diode CR5 is again shorted and provides a low impedance path to discharge capacitor C20.

The electronic metering device M1 is grounded to the ground plate at terminal 6. The meter M1 terminals 5 and 8 and terminals 9 and 10, respectively, are jumpered. Terminals 11, 12, and 13 of the meter M1 are connected to the switch section S1A1 whose wiper is connected to the positive terminal of the battery BT1 through on/off switch S2. Terminals 11, 12 and 13 of the meter determine the decimal placement of the displayed output. Terminals 3 and 6 of the switch section S1A1, corresponding to the 200 mA and percent of standard range, are shorted so that the meter operates in the same manner for these ranges.

A parts list for the circuit shown in FIGS. 5–7 is provided below. Also, the pin numbers shown in FIGS. 7A and 7B for the operational amplifiers U1, U2, U3, U4 and voltage regulator U5 relate to the parts specified in the list, although, of course, it is envisioned that components comparable to those listed below, connected differently from that shown in FIGS. 5–7, may be suitable for use.

| PARTS LIST FOR CIRCUIT SHOWN IN FIGS. 5–7 | |
|---|---|
| Part Description | Reference Designation |
| Resistor 296Ω | R1 |
| Resistor 715Ω | R2 |
| Resistor 604Ω | R3 |
| Resistor 169Ω | R4 |
| Resistor 374Ω | R5 |
| Resistor 422Ω | R6 |
| Resistor 2KΩ | R7 |
| Resistor 909Ω | R8 |
| Resistor 499Ω | R9 |
| Resistor 1MΩ | R10 |
| Resistor 68Ω | R11 |
| Resistor 300Ω | R12 |
| Resistor 300Ω | R13 |
| Resistor 2KΩ | R14 |
| Resistor 62Ω | R15 |
| Resistor 90.9Ω | R16 |
| Resistor 10Ω | R17 |
| Resistor 3.9KΩ | R18 |
| Resistor 1.5KΩ | R19 |
| Potentiometer 500Ω | R20 |
| Resistor 240Ω | R21 |
| Potentiometer 10KΩ | R22 |
| Potentiometer 500Ω | R23 |
| Resistor 24Ω | R24 |
| Resistor 1KΩ | R25 |
| Resistor 7.5KΩ | R26 |
| Resistor 4.7KΩ | R27 |
| Resistor 100KΩ | R28 |
| Resistor 4.99KΩ | R29 |
| Resistor 4.7KΩ | R30 |
| Resistor 4.99KΩ | R31 |
| Resistor 100KΩ | R32 |
| Resistor 100KΩ | R33 |
| Resistor 27KΩ | R34 |
| Resistor 220KΩ | R35 |
| Resistor 9.09KΩ | R36 |

PARTS LIST FOR CIRCUIT SHOWN IN FIGS. 5–7

| Part Description | Reference Designation |
| --- | --- |
| Resistor 1KΩ | R37 |
| Resistor 2KΩ | R38 |
| Capacitor .22 μF | C1 |
| Capacitor .0027 μF | C2 |
| Capacitor 33pF | C3 |
| Capacitor .0047 μF | C4 |
| Capacitor 47pF | C5 |
| Capacitor 75pF | C6 |
| Capacitor .033 μF | C7 |
| Capacitor .012 μF | C8 |
| Capacitor .1 μF | C9 |
| Capacitor 1 μF | C10 |
| Capacitor .1 μF | C11 |
| Capacitor .1 μF | C12 |
| Capacitor .1 μF | C13 |
| Capacitor .1 μF | C14 |
| Capacitor .1 μF | C15 |
| Capacitor 1 μF | C16 |
| Capacitor 1 μF | C17 |
| Capacitor 2.2 μF | C18 |
| Capacitor 22 μF | C19 |
| Capacitor 1 μF | C20 |
| Capacitor 10 μF | C21 |
| Thermistor 5KΩ | TH1 |
| Thermistor 5KΩ | TH2 |
| Thermistor 5KΩ | TH3 |
| 1/4 Operational Amplifier OP11A | U1 |
| 1/4 Operational Amplifier OP11A | U2 |
| 1/4 Operational Amplifier OP11A | U3 |
| Operational Amplifier LH0042 | U4 |
| IC Voltage Regulator 7905 | U5 |
| 1/4 Operational Amplifier OP11A | U6 |
| Transistor 2N4124 | Q1 |
| Transistor 2N4124 | Q2 |
| Diode 1N270 | CR1 |
| Diode 1N270 | CR2 |
| Diode 1N270 | CR3 |
| LED | CR4 |
| Diode 1N3595 | CR5 |
| Inductor .39 μH | L1 |
| Inductor 1.4 μH | L2 |
| Meter, Modutec BL100101 | M1 |
| Ganged Switch - four position, five switch sections | S1:S1A, S1B |
| On/Off Switch SPST | S2 |
| Push-button Switch SPST | 32 |
| Relay, Tri-Ridge Model No. 101-100 12 V | K1 |
| Rechargeable Battery 8.4 V | BT1 |

The contact hazard meter of the present invention provides an apparatus for measuring contact current which would flow through the human body to ground upon grasping an item carrying radio frequency, electromagnetic fields. The measurement can be taken quickly to determine whether the contact current is greater than maximum permissible exposure values as determined by safety guidelines. The contact hazard meter of the present invention minimizes the chance of RF shock and burns by determining a contact current prior to human contact with the item being monitored. The contact hazard meter of the present invention is portable and may be moved to whatever location tile operator desires.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A contact hazard metering device for measuring electromagnetic currents which would flow from an item carrying field induced currents to ground through a human body in physical contact with the item, which comprises:

a contact gun assembly, the contact gun assembly having an electrically non-conductive housing and a conductive contact mounted on the housing and placeable against an item for measuring field induced currents carried by the item;

a human equivalent circuit, the human equivalent circuit being electrically coupled to the conductive contact, the human equivalent circuit being formed of a plurality of electrical components interconnected and having values to approximate the impedance of a human body at varying frequencies;

a current sensing resistor, the current sensing resistor being coupled between the human equivalent circuit and ground, wherein field induced current flowing from the item through the conductive contact and human equivalent circuit flows through the sensing resistor to cause a corresponding voltage to be impressed across the sensing resistor;

at least a first sensing diode, the first sensing diode being coupled to the sensing resistor and being responsive to the voltage impressed across the sensing resistor to generate an output voltage signal corresponding to the voltage across the sensing resistor, the first sensing diode operating in the square law region;

a current measuring circuit, the current measuring circuit being coupled to the first sensing diode and including a square root circuit, the square root circuit being responsive to the output signal of at least the first sensing diode and generating an output signal in response thereto; and display means for displaying a measurement of the field induced current flowing through the human equivalent circuit, the display means being coupled to the current measuring circuit and being responsive to the output signal thereof.

2. A contact hazard metering device as defined by claim 1, which further comprises means to selectively measure a finite time period of current flowing through the human equivalent circuit, the finite time period current measuring means including:

a timing circuit, the timing circuit including a switch, the switch being mounted on the housing of the contact gun assembly, the timing circuit generating a timing signal in response to actuation of the switch;

a relay, the relay being selectively electrically coupled in series with the human equivalent circuit, the relay being responsive to the timing signal generated by the timing circuit and being in one of a first state and second state in response thereto, the relay being effectively an open circuit and not allowing current to flow through the human equivalent circuit when the relay is in the first state, the relay being effectively a short circuit and allowing current to flow through the human equivalent circuit when the relay is in the second state; and a peak hold circuit, the peak hold circuit being selectively electrically coupled to and interposed between the current measuring circuit and the display means, the peak hold circuit being further coupled to the timing circuit and including a storage device, the storage device selectively storing a charge therein corresponding to the current flowing through the human equivalent circuit, the peak hold circuit generating an output signal corresponding to the charge stored in the storage device, the display means being responsive to the output signal of the peak hold circuit to display a measurement of the field induced current flowing through the human equivalent circuit.

3. A contact hazard metering device as defined by claim 1, which further comprises a frequency shaping circuit, the frequency shaping circuit being coupled to the sensing resistor and providing an output signal corresponding and in response to the voltage impressed across the sensing resistor, the output signal corresponding to the field induced current flowing through the human equivalent circuit, the output signal varying linearly as a function of the electromagnetic field frequency up to a predetermined frequency and being constant and independent of frequency above the predetermined frequency, the output signal of the frequency shaping circuit being provided to the first sensing diode.

4. A contact hazard metering device as defined by claim 3, wherein the output signal of the frequency shaping circuit corresponds to the field induced current, I, where:

$$I = 1000 \times f, \text{ in mA for } 0.003 \leq f \leq 0.1 \text{ MHz},$$

and $$I = 100 \text{ mA for } f > 0.1 \text{ MHz},$$

where f is the frequency of the electromagnetic field.

5. A contact hazard metering device for measuring electromagnetic currents, which comprises:
   a conductive contact placeable against an item for measuring field induced currents carried by the item;
   a human equivalent circuit electrically coupled to the conductive contact, the human equivalent circuit providing an impedance approximating the impedance of a human body; and
   an electronic circuit coupled to the human equivalent circuit, the electronic circuit measuring the current flowing from the item being monitored through the human equivalent circuit to ground.

6. A contact hazard metering device as defined by claim 5, wherein the electronic circuit includes a meter for displaying a measurement of the current flowing from the item through the human equivalent circuit to ground.

7. A contact hazard metering device as defined by claim 6, further comprising means for mounting the human equivalent circuit, the electronic circuit and the meter.

8. A contact hazard metering device as defined by claim 7, wherein the mounting means comprises a ground plate for suppressing potential and scalar fields, the ground plate having an upper and lower surface, the lower surface being placeable on the ground in proximity to the item, the human equivalent circuit and electronic circuit being mounted on the upper surface of the ground plate.

9. A contact hazard metering device as defined by claim 8, which further comprises a housing, the housing being mounted on the upper surface of the ground plate; and wherein the human equivalent circuit, electronic circuit and meter are positioned within the housing.

10. A contact hazard metering device as defined by claim 9, wherein the housing includes a shielded section and an unshielded section, the meter and electronic circuit being mounted within the shielded section, the human equivalent circuit being mounted within the unshielded section.

11. A contact hazard metering device as defined by claim 5, wherein the electronic circuit includes a current range select switch having a plurality of positions for selecting various ranges of measured field induced currents.

12. A contact hazard metering device as defined by claim 5, wherein the electronic circuit further includes a timing circuit, the timing circuit comprising:
    a relay having a first state and a second state, the relay being electrically coupled to the human equivalent circuit; and
    a switch electrically coupled to the relay and being positionable in a first position and a second position, wherein the relay is responsive to the switch position so that the relay is in the first state when the switch is in the first position and the relay is in the second state when the switch is in the second position, the relay being effectively an open circuit and allowing no current to flow through the human equivalent circuit when the relay is in the first state, and the relay being effectively a short circuit and allowing current to flow through the human equivalent circuit when the relay is in the second state.

13. A contact hazard metering device as defined by claim 12, wherein the electronic circuit further includes a peak hold circuit, the peak hold circuit including a storage device, the peak hold circuit being responsive to the switch, the storage device storing a charge corresponding to the current flowing through the human equivalent circuit when the switch is in the second position, the peak hold circuit measuring the charge stored in the storage device.

* * * * *